(12) United States Patent
Wukasch et al.

(10) Patent No.: US 8,968,218 B2
(45) Date of Patent: Mar. 3, 2015

(54) GAIT SYMMETRY MEASUREMENT AND IMPROVEMENT

(75) Inventors: Matthew P. Wukasch, Davie, FL (US); Jose M. Hernandez, Jr., Miramar, FL (US)

(73) Assignee: Interactive Metronome, Inc., Sunrise, FL (US)

( * ) Notice: Subject to any disclaimer, the term of this patent is extended or adjusted under 35 U.S.C. 154(b) by 1015 days.

(21) Appl. No.: 12/703,353

(22) Filed: Feb. 10, 2010

(65) Prior Publication Data

US 2010/0217159 A1    Aug. 26, 2010

Related U.S. Application Data

(60) Provisional application No. 61/151,663, filed on Feb. 11, 2009.

(51) Int. Cl.
*A61B 5/103* (2006.01)
*A61B 5/117* (2006.01)
*A61B 5/11* (2006.01)
*A61B 5/00* (2006.01)

(52) U.S. Cl.
CPC .............. *A61B 5/1038* (2013.01); *A61B 5/112* (2013.01); *A61B 5/486* (2013.01); *A61B 5/6829* (2013.01)
USPC .......................................... 600/595; 600/587

(58) Field of Classification Search
USPC .......................................... 600/587, 592, 595
See application file for complete search history.

(56) References Cited

U.S. PATENT DOCUMENTS

| | | | |
|---|---|---|---|
| 4,387,437 A * | 6/1983 | Lowrey et al. | 702/160 |
| 4,919,030 A | 4/1990 | Perron, III | |
| 5,529,498 A | 6/1996 | Cassily et al. | |
| 5,743,744 A | 4/1998 | Cassily et al. | |
| 6,645,126 B1 | 11/2003 | Martin et al. | |
| 6,719,690 B1 | 4/2004 | Cassily | |
| 7,122,004 B1 | 10/2006 | Cassily | |
| 7,997,007 B2 * | 8/2011 | Sanabria-Hernandez | 36/1 |
| 2007/0204687 A1 * | 9/2007 | Haselhurst et al. | 73/172 |
| 2009/0240171 A1 * | 9/2009 | Bamberg et al. | 600/595 |
| 2010/0075806 A1 * | 3/2010 | Montgomery | 482/8 |
| 2011/0184225 A1 * | 7/2011 | Whitall et al. | 600/28 |

* cited by examiner

*Primary Examiner* — Adam Eiseman
(74) *Attorney, Agent, or Firm* — Gardner, Linn, Burkhart & Flory, LLP

(57) ABSTRACT

A gait-enhancing system and method of enhancing gait includes generating a reference signal having substantially equal durations between occurrences and providing the reference signal to a user. Contact between the feet of the user with a surface is received and occurrence of a trigger signal is generated in response to the contact. An occurrence of the trigger signal is compared with an occurrence of a reference signal, and a guidance signal is produced as a function of the amount of time that the trigger signal led or lagged the reference signal. The guidance signal is provided to the user in order to promote symmetry in stride between one foot and the other foot of the user, enhancing the user's gait.

24 Claims, 8 Drawing Sheets

GAIT SYMMETRY MEASUREMENT AND IMPROVEMENT

CROSS REFERENCE TO RELATED APPLICATIONS

This application claims priority from U.S. provisional patent application Ser. No. 61/151,663 filed Feb. 11, 2009, the disclosure of which is hereby incorporated herein by reference in its entirety.

BACKGROUND OF THE INVENTION

The present invention is directed to a method of enhancing gait and a gait-enhancing system.

A user's gait is a description of the activities performed by the user undergoing locomotion. In particular, gait refers to the user's walking ability, although it could also be used to describe a running motion. Walking requires a complex movement involving weight shift, as well as cadence and stride length. Various techniques have been disclosed for performing gait analysis. Because of the complexity of the walking motion, most such gait analysis labs calculate movement kinesthetics utilizing complex equipment, such as floor load transducers, and the like. Also, such systems merely analyze gait and do not typically provide a technique for improvement to the gait.

SUMMARY OF THE INVENTION

The present invention is directed to a technique for both measuring and enhancing a user's gait. This is accomplished with a system that is easy to use and provides freedom and flexibility to the user.

A gait-enhancing system and method of enhancing gait, according to an aspect of the invention, includes generating a reference signal having substantially equal durations between occurrences and providing the reference signal to a user. Contact between the feet of the user with a surface is received and occurrence of a trigger signal is generated in response to the contact. An occurrence of the trigger signal is compared with an occurrence of a reference signal, and a guidance signal is produced as a function of the amount of time that the trigger signal led or lagged the reference signal. The guidance signal is provided to the user in order to promote symmetry in stride between one foot and the other foot of the user, enhancing the user's gait.

A gait-enhancing system and method of enhancing of gait, according to another aspect of the invention, includes providing a pair of remote units, each having a sensor that is configured to the sole of one of the user's feet and a remote wireless transceiver that is functionally connected with the sensor. Each of the remote wireless transceivers is configured to mount with a portion of the user's leg or foot. A processing unit is provided with a local wireless transceiver that is functionally connected with the processing unit. The processing unit generates a reference signal and provides the reference signal to the user. The reference signal has substantially equal duration between occurrences. The gait of the user is monitored with the remote units including generating occurrences of a trigger signal in response to the sensors contacting a surface. The occurrence of the trigger signal is transmitted with the remote wireless transceiver to the local wireless transceiver. The processing compares occurrence of the trigger signal with an occurrence of the reference signal and produces a guidance signal as a function of an amount of time that the trigger signal led or lagged the reference signal. The guidance signal is provided to the user in order to promote symmetry in stride between one foot and the other foot of the user to enhance user gait.

The promotion of symmetry in stride between one foot and the other of the user provides enhancement to the user gait which may be used to increase the cadence of the user over time.

These and other objects, advantages and features of this invention will become apparent upon review of the following specification in conjunction with the drawings.

DESCRIPTION OF THE PREFERRED EMBODIMENT

Figure 1:
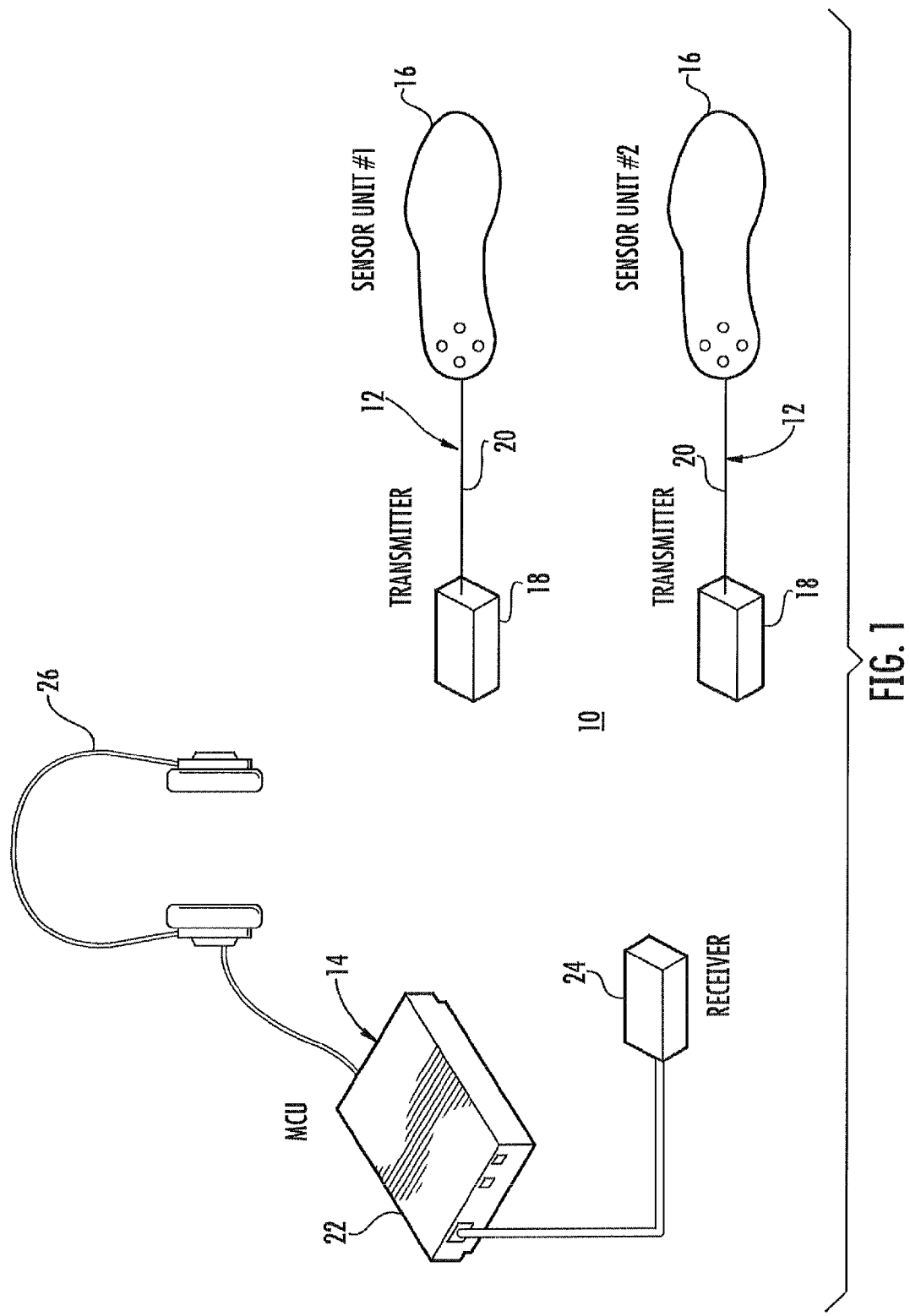
FIG. 1 is directed to a block diagram of a gait-enhancing system, according to an embodiment of the invention.

Referring now specifically to the drawings, and the illustrative embodiments depicted therein, a gait-enhancing system 10 includes a pair of remote units 12 and a local unit 14 (FIG. 1). Each remote unit 12 includes a sensor 16 that is configured generally to the sole of one of the user's feet and a remote wireless transceiver 18 that is functionally interconnected with sensor 16, such as with a flexible cable 20. Local unit 14 includes a processing unit 22 and a local wireless transceiver 24. Each remote transceiver 18 is designated a transmitter because its primary function is to transmit signals to local transceiver 24. In a similar fashion, local transceiver 24 is designated a receiver because its primary function is to receive signals transmitted by remote transceivers 18. However, it should be understood that transceivers 18 and 24 are all capable of both transmitting and receiving signals and all receive signals transmitted by the other transceivers. Local unit 14 additionally includes an audio output device 26 in order to supply audio signals produced by processing unit 22 to a user. Audio output device 26 may be a set of headphones, as illustrated in FIG. 1. Alternatively, the audio output device may be one or more broadcast speakers, which may provide audio signals not only to the user, but to a therapist, or the like.

In use, processing unit 22 produces a reference signal having a substantially equal duration between occurrences of the reference signal. The reference signal is supplied to the user via audio output device 26. Each of the remote units 12 detects contact between a respective foot of the user and a surface, such as a gymnasium floor, or the like. Each remote unit 12 generates an occurrence of a trigger signal in response to the respective sensor 16 making contact with the surface. Remote transceiver 18 wirelessly transmits the trigger signal to local transceiver 24 which provides the trigger signal to processing unit 22. Processing unit 22 compares the occurrence of the trigger signal with an occurrence of the internally generated reference signal and produces a guidance signal as a function of the amount of time that the trigger signal led or lagged the reference signal. The guidance signal is provided to the user via audio output device 26. As disclosed in commonly assigned U.S. Pat. Nos. 5,529,498; 5,743,744; 6,719,690; and 7,122,004 issued to Cassily et al., the disclosures of which are hereby incorporated herein by reference in their entirety, the guidance signal supplied to the user tends to draw the user to the reference signal. This causes the user to subconsciously bring the user's feet into alternating contact with the surface at closer and closer times to the reference signal. Because the reference signal has substantially equal duration between occurrences, this draws the user into a cadence that approaches the reference signal. This promotes symmetry of stride between one foot of the user and the other foot of the user to enhance the user's gait. The promotion of symmetry in stride between the feet of the user may enhance stride length, heel strike, gait stamina, weight shifting and overall quality movement of the user. As will be set forth in more detail below, this may be accomplished by a relatively easy-to-use system that only monitors contact between the user's foot and the surface without requiring a complex analysis of the forces generated by the foot, or the like.

Figure 2:
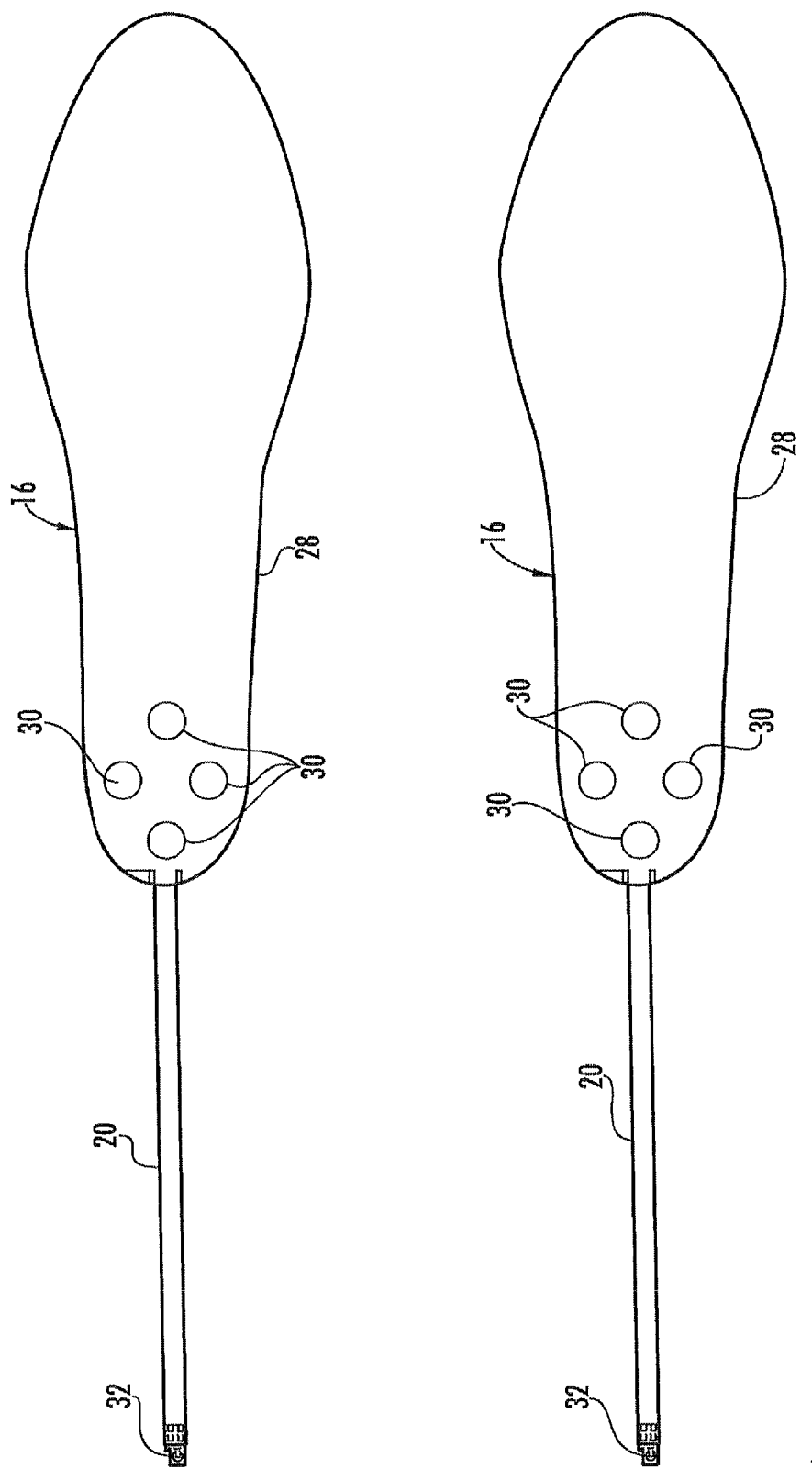
FIG. 2 is a diagram of a pair of sensors that are useful with the invention.
Figure 3:
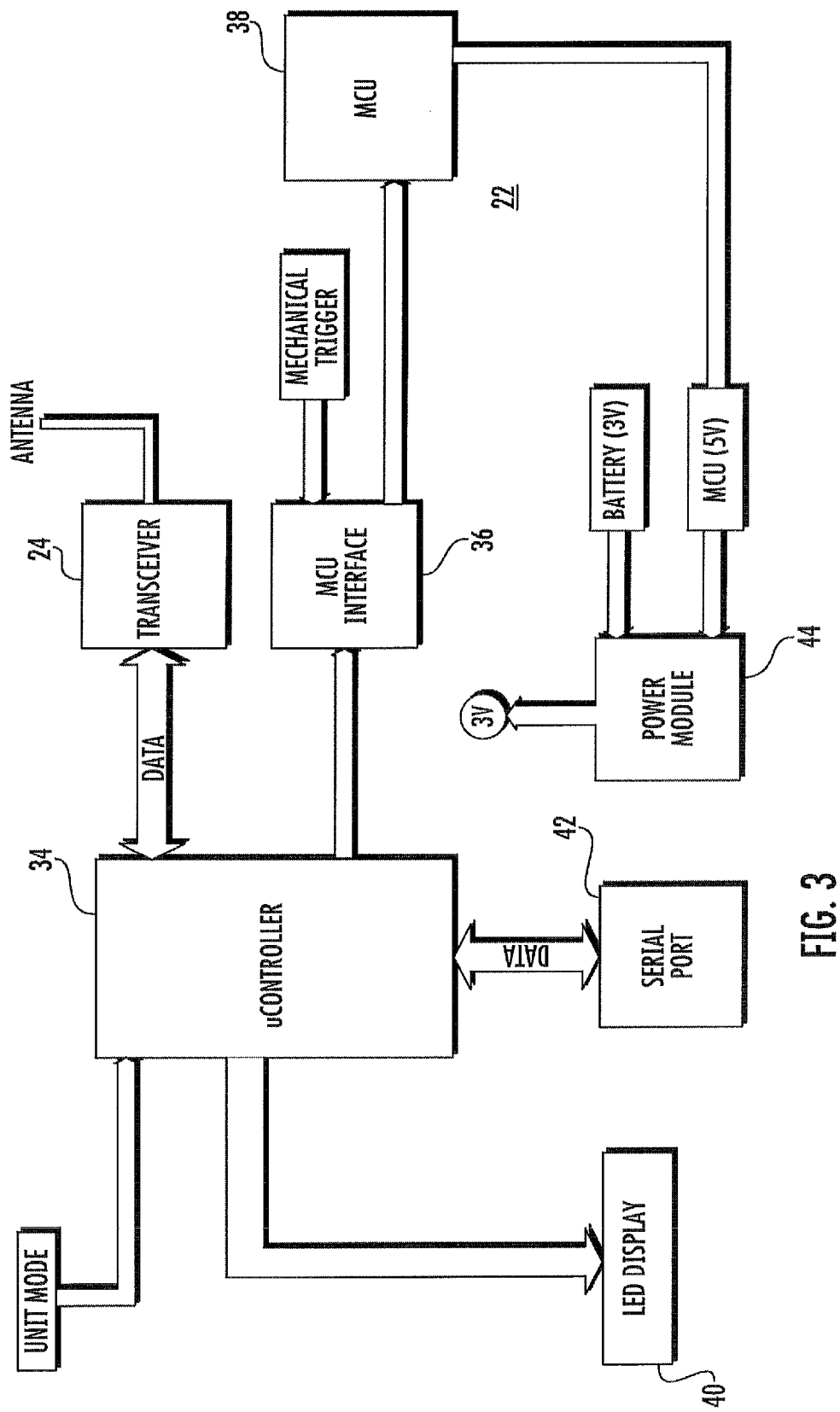
FIG. 3 is a block diagram of a main control unit.

Details of sensor 16 can be seen by reference to FIG. 2 in which the sensor includes an insole 28 and a plurality of switches 30 embedded in insole 28. Switches 30 are mechanical contact switches of the type known in the art for use with keyboards, and the like, but may be other types of switches. Switches are individually electrically connected through flexible cable 20 to a connector 32 that engages with a mating connector (not shown) of the respective remote transceiver 18. Sensor 16 may be configured to the foot of the user, such as by trimming insole 28 to fit within the shoe of the user. Thus, it is not necessary to supply sensor 16 in a wide variety of sizes. Of course, it would also be possible to supply sensor 16 in multiple different sizes. In the illustrative embodiment, remote transceiver 18 is configured to strap onto the distal leg of the user, such as in the region of the ankle, with flexible cable 20 allowing relatively free movement of sensor 16 as the user creates the walking action. In the illustrative embodiment, flexible cable 20 is a ribbon cable, but other forms may be used.

Processing unit 22 includes a microcontroller 34 of the type that is well known in the art. Microcontroller 34 is programmed to set the command registers of local transceiver 24 in order to configure its operational parameters. Microcontroller 34 is also programmed to retrieve and send messages through local transceiver 24. Processing unit 22 further includes an MCU interface 36 that interfaces with an MCU 38 that generates the reference signals and guidance signals and supplies the signals to the audio output device 26 utilizing the techniques described in the Cassily et al. patents. When a trigger message is received, microcontroller 34 will generate a discrete signal to the MCU, thus signaling an occurrence of a trigger event. Through MCU interface 36, microcontroller 34 may also monitor an optional external mechanical switch (not shown) that, when activated, will also generate an occurrence of the trigger signal to the MCU. Microcontroller 34 will also generate visual signals by turning on or off two or more LEDs of an LED display 40. A serial port 42 may be used in order to provide programming instructions, or the like, to microcontroller 34.

Figure 5:
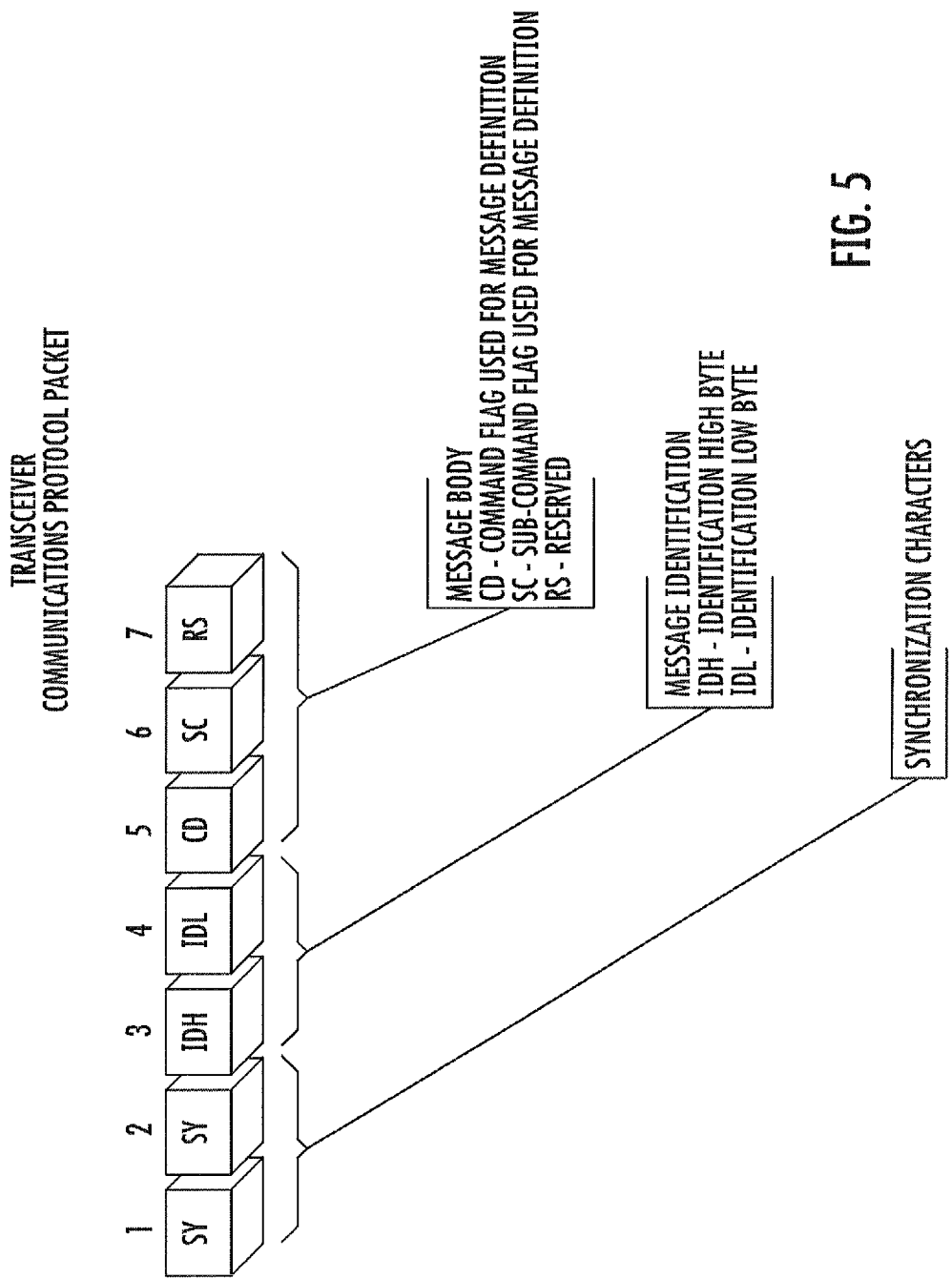
FIG. 5 is a diagram of a communication protocol packet.
Figure 6:
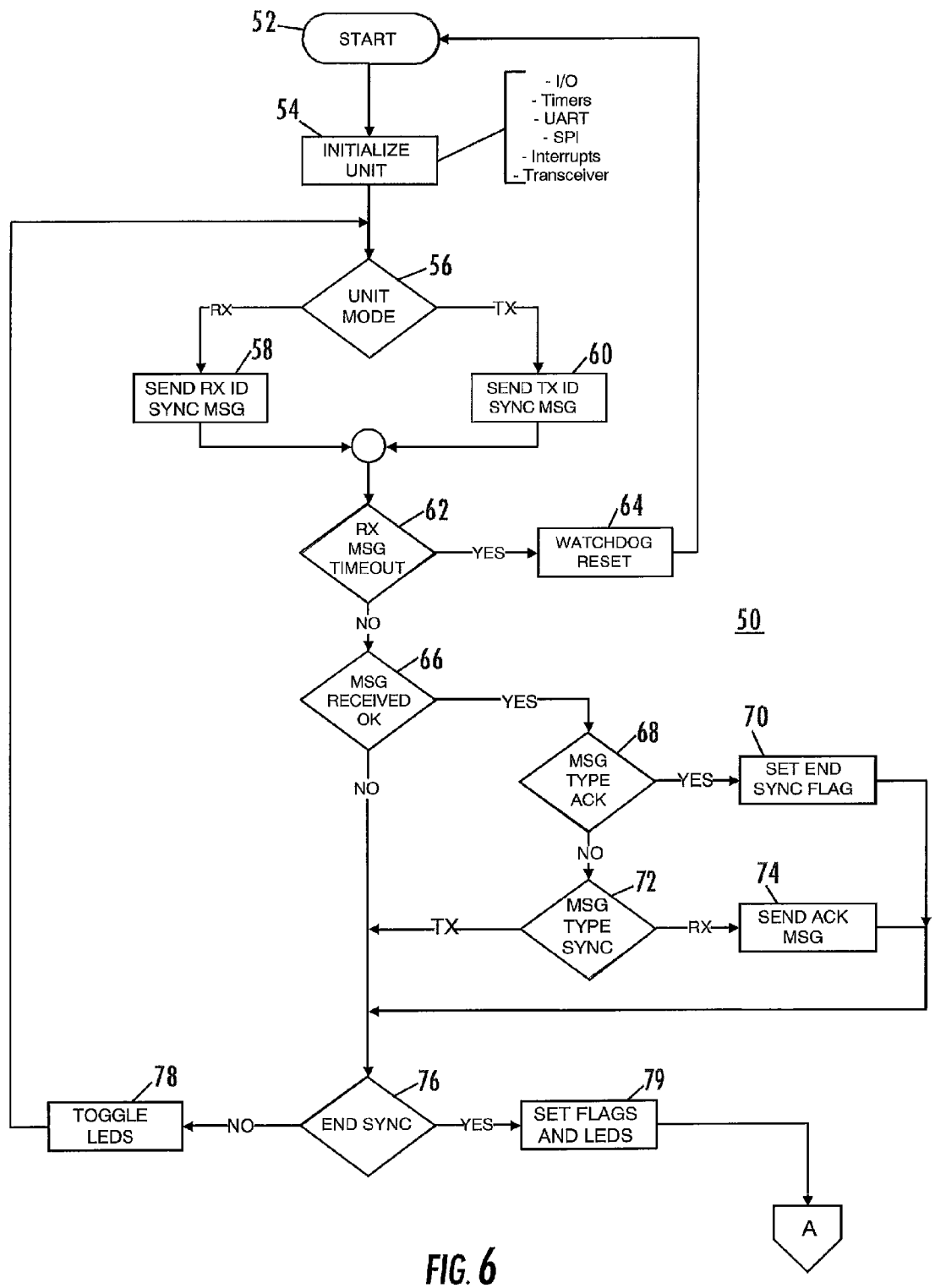
FIG. 6 is a flowchart of an initialization and synchronization function.

Local transceiver 24 is capable of transmitting and receiving information packets wirelessly with a comparable transceiver. The protocol format is illustrated in FIG. 5. Transceiver 24 is controlled by microcontroller 34 by providing it with operational setup commands. In addition, transceiver 24 notifies the microcontroller when a message is received or transmitted. A power module 44 is capable of drawing power from either batteries or from a physical connection to MCU 38. Only one power source is used at a time.

The transceiver communication protocol packet illustrated in FIG. 5 is made up of seven bytes of information. The first two bytes of the message are synchronization characters that may be used by the transceiver hardware for identifying a new message stream and clock recovery phase. The second set of bytes of the message provides the identification number of the message. This identification number is used by the transceiver to determine if the message is addressed for that unit. If the identification number matches those programmed within the transceiver, the message is then processed. Otherwise, it is discarded. The next three bytes of the message contain the body of the message. The first byte represents the command being issued to the unit or the command being sent from the unit. Byte number 6 contains an additional subcommand that allows for further refinement of the command being issued. The last byte of the message may be reserved for other purposes.

Figure 4:
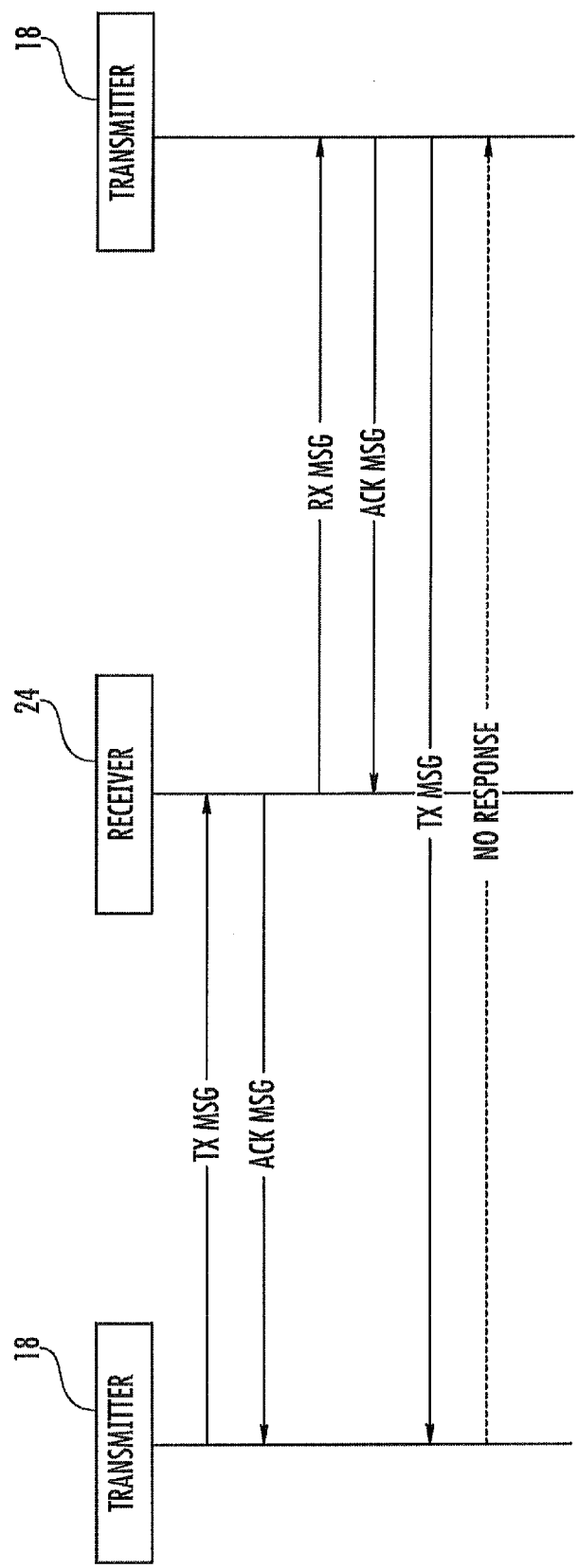
FIG. 4 is a signal flow diagram between the main control unit and the remote units.

As set forth above, remote transceivers 18 are designated as transmitters although they are capable of both transmitting and receiving. Likewise, local transceiver 24 is cable of both transmitting and receiving, but is designated as a receiver. Referring to FIG. 4, when power is applied to the unit, the unit will initialize its internal parameters, activate a watchdog timer and enter into a state of synchronization. Synchronization can only be achieved from a unit of different configuration, namely, local transceiver 24 (receiver) and a remote transceiver 18 (transmitter). Synchronization is not authenticated between transmitter units 18. Synchronization is achieved when an acknowledgement message (ACK) is received from another unit of different configuration. If no message is received at a predetermined time, the unit's watchdog timer expires and a full reset condition occurs. Thus, a transmitter 18 sending a transmitter identification (TX) message receives an ACK message from receiver 24. Likewise, a receiver identification (RX) message from receiver 24 results in an ACK message from a transmitter 18. However, a TX message from a transmitter does not elicit a response from the other transmitter 18.

After synchronization is achieved, the units will enter normal operation. When in normal operation, each transmitter 18 will sample the input signals from sensor 16 in order to report any trigger occurrences. If a trigger signal occurs, a trigger message (TRG) is transmitted. If no trigger occurrences are recorded within a predetermined time, the remote unit will send a transmitter identification (TX) message to ensure synchronization with the receiver unit. In normal operating mode, receiver 24 will monitor incoming messages. If a trigger (TRG) message is received in the proper format, receiver 24 will generate an electrical stimulus for MCU 38 signaling the occurrence of a trigger signal. An ACK message will be transmitted back to the sending transmitter 18. If the receiver 24 receives a transmitter identification (TX) message, the receiver transmits an ACK message allowing synchronization to occur. If no activities are recorded for a predetermined time, receiver 24 will transmit a receiver identification (RX) message to stimulate synchronization with transmitters 18.

An initialization and synchronization function 50 begins at 52 by performing an initialization routine 54 in order to write stored information to microcontroller 34. It is then determined at 56 whether the particular unit on which the computer software is running is a receiver 24 or a transmitter 18. If it is determined at 56 that the unit is a receiver 24, the unit sends a receiver identification (RX) message at 58. If it is determined at 56 that the unit is a transmitter, it sends a transmit identification (TX) message at 60. A unit determines whether it is a receiver or a transmitter in the illustrated embodiment by a hardware variation. Otherwise, in the illustrative embodiment, each unit's microcontroller runs the same computer program whether the unit is a transmitter or a receiver. If it is determined at 62 that the receiver did not receive a message within a particular period of time, a watchdog reset occurs at 64. If it is determined at 62 that the timeout has not yet occurred, it is determined at 66 whether the received message is correctly formatted. If it is, it is determined at 68 whether the message was an acknowledge (ACK) message. If so, synchronization has been established for that unit and an end of synchronization flag is set at 70. If it is determined at 68 that the received message was not an ACK message, it is determined at 72 whether the unit is a transmitter or receiver. If it is a receiver, the unit sends an acknowledge (ACK) message at 74. It is then determined at 76 whether synchronization has been achieved. If not, a particular pattern is displayed with LED display 40 at 78. If synch has been achieved, a flag is set at 79 and a different pattern of LEDs are illuminated on display 40.

Figure 7:
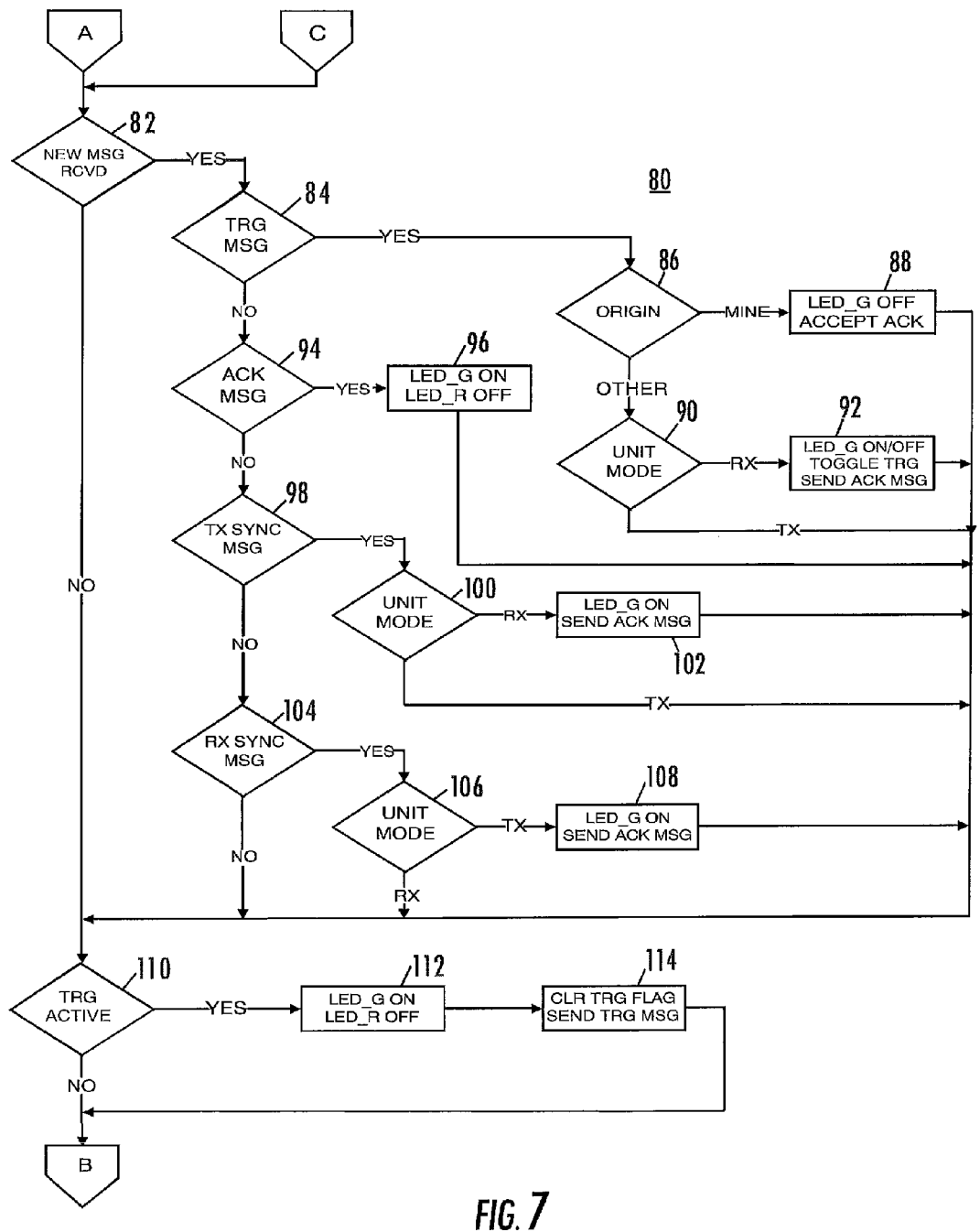
FIG. 7 is a flowchart of a message processing function.

After synchronization has been achieved, a message processing function 80 is carried out (FIG. 7). A message function is processed beginning at 82 by determining whether a new message has been received. If so, it is then determined at 84 whether the message is an occurrence of a trigger signal. If so, it is then determined at 86 whether the unit was merely receiving a signal sent by itself. If so, a particular pattern of LEDs are displayed on display 40 at 88. If it is determined at 86 that the unit is not its own source of the trigger message, it is determined at 90 what type of unit received the trigger message. If it is a receiving unit, a particular sequence of LEDs is displayed and the receiver sends an ACK message at 92. If it is determined at 90 that the unit is a transmitter, no action is taken.

If it is determined at 84 that the received message is not a trigger message, it is determined at 94 whether the received message is an acknowledge (ACK) message. If so, a particular pattern of LEDs are displayed with display 40 at 96. If it is determined at 94 that the message is not an acknowledge message, it is determined at 98 whether the message is a TX message which is a transmitter identification message requesting synchronization with the receiver. If so, it is determined at 100 whether the receiving unit is a transmitter or receiver. If it is receiver, a particular pattern of LEDs is illuminated by display 40 and an acknowledge message is sent at 102. If it is determined at 100 that the receiving unit is a transmitter, no action is taken. If it is determined at 98 that the incoming message is not a transmit identification (TX) message, it is determined at 104 whether the incoming message is a receiver identification (RX) synchronization message. If so, it is determined at 106 whether the receiving unit is a transmitter or a receiver. If it is a transmitter, a particular pattern of LEDs are displayed on display 40 and an acknowledge message is sent at 108. If it is determined at 104 that the message received was not an RX synchronization message, then no action is taken.

Figure 8:
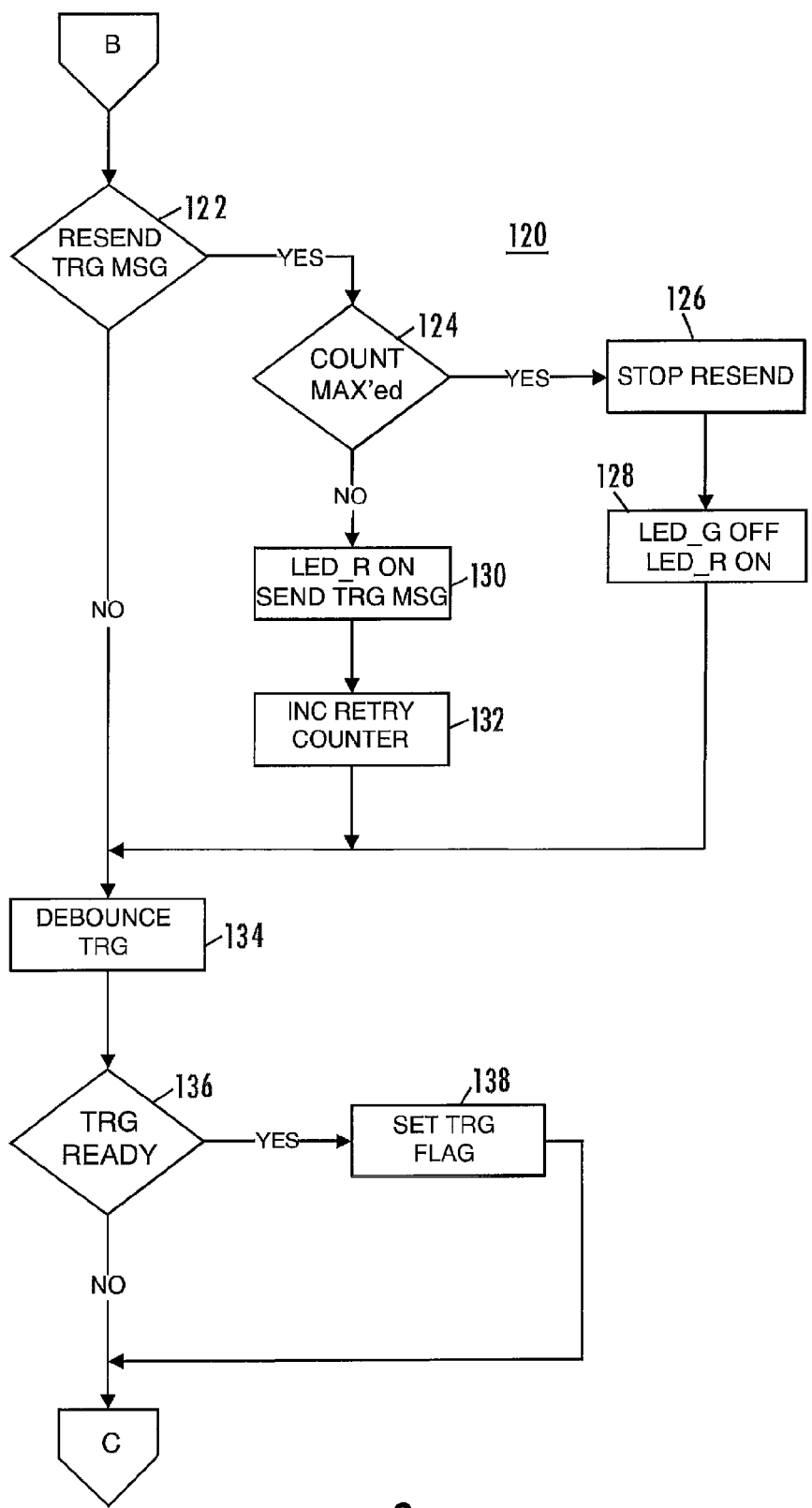
FIG. 8 is a flow diagram of a trigger processing function.

Control then passes to 110 where it is determined whether a trigger event has occurred. If it has, the unit displays a particular pattern of LEDs on display 40 at 112 and clears the trigger flag and sends a trigger message at 114 to the MCU. Control then passes to a trigger check function 120 (FIG. 8). The function begins at 122 by determining whether it is necessary to resend a trigger (TRG) message. A trigger message is resent if an acknowledge message has not been received from a previously sent trigger message. If the trigger message must be resent, it is determined at 124 whether the time limit for resending the trigger message has been exceeded. If so, then the unit stops resending the trigger message at 126 and displays a particular pattern of LEDs on display 40 at 128. If it is determined at 124 that the time limit has not been exceeded, a particular pattern of LEDs are illuminated on display 40 and the trigger message is resent at 130. The retry counter that is examined at 124 is incremented at 132. In the illustrative embodiment, the sending of the trigger message initiates the timer. If the acknowledge is not received within up to three tries, the unit stops resending the trigger message. As will be discussed in more detail below, the unit is configured to send a trigger message within a particular period of time, such as 1 millisecond, of receiving the actuation of a sensor 16 and all units are configured to have approximately the same delay built into the sending of the trigger message. Thus, with a 1 millisecond delay, there should be no more than a 3 millisecond delay for repeating of the trigger signal. However, it should be understood that these parameters are for illustration purposes only and other parameters may be used.

If it is determined at 122 that it is not necessary to resend the trigger message, a debounce routine 134 is performed on switches 30. The debounce routine is in order to ensure that no more than one trigger message is generated for each contact between a foot and a surface. In the illustrative embodiment, the debounce routine makes sure that all four of switches 30 in sensor 16 are open, or are deactuated, before recognizing a new trigger event. Once it is determined that all of the switches are again open, it is determined at 136 whether a new trigger event has occurred. If so, a trigger flag is set at 138.

In the illustrative embodiment, switches 130 are provided as separate inputs to the microcontroller in respective remote unit 12. In order to ensure a brief and uniform delay between actuation of one of the switches 30 and generation of a trigger signal, switches 30 are provided as interrupt inputs to the respective microcontroller. Therefore, the respective controller discontinues any activities being carried on in the background and immediately processes the actuation of the switch 30. Because actuation of a switch 30 results in virtually instantaneous recognition by the corresponding microprocessor and because a fixed delay is built into the program of the microprocessor between the actuation of the switch and sending of the trigger signal, there is a uniform delay between actuation of one of the sensors 16 and receipt of the trigger at local unit 14. As previously set forth, local unit 14 compares the trigger signal with generation of the reference signal and determines whether the foot contact led or lagged the reference signal. Depending upon the result of this determination, a particular audio signal is sent to audio output device 26 in the manner disclosed in the previously referred to Cassily et al. patents. Thus, the guidance sounds may be based upon a delay between actuation of a sensor 16 and receipt of that trigger signal of local unit 14. However, the delay will be virtually identical for both the right foot and the left foot. Because the delay is virtually identical, the mind of the user is able to ignore this delay in subconsciously processing the guide signal. It is only uneven and variable delay that would result in potential confusion to the user's subconscious processing of the guidance signal.

Because date-enhancing system 10 provides for wireless connection between the remote units 12 which are wore on the body of the user and the local unit, which may be located a distance from the user, the user is able to walk around freely without any physical interconnection with the local unit. This allows the user to walk around an auditorium, or the like, unfettered. This results in a more natural gait.

However, it should be understood that the gait-enhancing system technique disclosed herewith may also be applied in other settings. For example, a fixed contact sensor may be positioned, for example, on a treadmill below the moving belt. This would allow the processing unit to receive trigger signals directly from the fixed sensor. The processing unit may be positioned in the treadmill and may even share a common electronic unit with the treadmill control. As such, it is possible to provide either a hard-wired or a wireless interconnection between the foot switches and the processing unit. In such an embodiment, the cadence established by the reference signal may be adjustable in relationship to the speed set for the treadmill. Thus, as the treadmill is operated at a faster speed, the reference signal would be increased in repetition rate causing the user to walk at a corresponding faster pace. It may be necessary to also provide an input for the stride length for the user which, of course, varies with the size of the user, and the like.

By enhancing symmetry in the gait, the user is able to develop a stronger gait. As the user achieves further enhancement in his or her gait, the repetition rate of the reference signal can be increased in order to encourage the user to walk at a faster pace. Thus, the various embodiments of the invention are able to correct the gait of users who have gait difficulties, such as Parkinson patients, and the like. The embodiments disclosed herein are also capable of enhancing the gait of a user having a relatively normal gait by making that gait stronger.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A method of enhancing gait of a user, comprising:
    mounting a pair of remote units to the user, each of said remote units having a sensor that is configured to a size of the sole of one of the user's feet;
    generating a reference signal with a processing unit and providing the reference signal to the user, the reference signal having substantially equal duration between occurrences;
    monitoring the gait of the user with said remote units including generating occurrences of a trigger signal in response to the sensors contacting a surface and providing the occurrences of the trigger signal to said processing unit;
    comparing an occurrence of the trigger signal with an occurrence of the reference signal and producing a guidance signal as a function of an amount of time that the trigger signal led or lagged the reference signal, said comparing and said producing carried out with said processing unit; and
    providing the guidance signal to the user to subconsciously bring the user's feet into alternative contact with the surface at closer times to the reference signal to draw the user into a cadence that approaches the reference signal in order to promote symmetry in stride between one foot and the other foot of the user to enhance user gait wherein said sensor includes a plurality of switches and wherein generating an occurrence of the trigger signal includes operation of any one of said switches including ignoring operation of other of said switches until said one of said switches is no longer operated wherein all said switches are deactivated before a new occurrence of the trigger signal is generated.

2. The method as claimed in claim 1 including configuring said sensor to match the size of the sole of the foot of the user.

3. The method as claimed in claim 2 wherein said sensor includes an insole for positioning within a shoe of the user and wherein said configuring includes trimming the insole to fit within the shoe of the user.

4. The method as claimed in claim 1 wherein said providing the reference signal and providing the guidance signal are carried out with at least one broadcast speaker or a set of headphones.

5. The method as claimed in claim 1 wherein each of said remote units includes a remote wireless transceiver that is functionally connected with said sensor and wirelessly transmitting the occurrences of the trigger signal with said remote wireless transceiver to a local wireless transceiver functionally connected with said processing unit.

6. The method as claimed in claim 5 wherein said transmitting the occurrences of the trigger signal includes providing a substantially constant delay between each of the sensor units contacting a surface and said transmitting the occurrences of the trigger signal.

7. The method as claimed in claim 6 wherein each of said remote units and said processing unit comprise a programmable controller and program code stored on a non-transient computer readable media, said program code operating the programmable controller, wherein the same program code is used with said processing unit with each of said remote units.

8. The method as claimed in claim 5 wherein said processing unit synchronizes with each of said sensor units.

9. The method as claimed in claim 8 wherein said processing unit confirms receipt of a trigger signal from one of said sensor units.

10. The method as claimed in claim 9 wherein each of said remote units receives a trigger signal from the other of said remote units but does not confirm receipt of the received trigger signal.

11. The method as claimed in claim 5 wherein each of said remote wireless transceivers is configured to mount to a portion of the user's leg or foot.

12. The method as claimed in claim 1 wherein said switches comprise mechanical switches.

13. A gait-enhancing system, comprising:
    a pair of remote units, each having a sensor that is configured to a size of the sole of one of the user's feet;
    a processing unit, said processing unit generating a reference signal and providing the reference signal to the user, the reference signal having substantially equal duration between occurrences;
    the remote units monitoring the gait of the user and generating occurrences of a trigger signal in response to the sensors contacting a surface, said remote units further providing occurrences of the trigger signal to said processing unit;
    said processing unit comparing an occurrence of the trigger signal with an occurrence of the reference signal and producing a guidance signal as a function of an amount of time that the trigger signal led or lagged the reference signal; and
    wherein the guidance signal is provided to the user to subconsciously bring the user's feet into alternative contact with the surface at closer times to the reference signal to draw the user into a cadence that approaches the reference signal in order to promote symmetry in stride between one foot and the other foot of the user wherein said sensor includes a plurality of switches and wherein an occurrence of the trigger signal is generated in response to operation of any one of said switches wherein said processing unit ignores operation of other of said switches until said one of said switches is no longer operated wherein all said switches are deactivated before a new occurrence of the trigger signal is generated.

14. The system as claimed in claim 11 wherein said sensor is configurable to match a size of the foot of the user.

15. The system as claimed in claim 14 wherein said sensor includes an insole for positioning within a shoe of the user and wherein said insole can be trimmed to fit within the shoe of the user.

16. The system as claimed in claim 11 including at least one broadcast speaker or a set of headphones to provide the reference signal and the guidance signal to the user.

17. The system as claimed in claim 11 wherein each of said remote units includes a remote wireless transceiver that is functionally connected with said sensor and wirelessly transmitting the occurrences of the trigger signal with said remote wireless transceiver to a local wireless transceiver functionally connected with said processing unit.

18. The system as claimed in claim 17 wherein said remote unit provides a substantially constant delay between each of the sensor units contacting a surface and transmitting the occurrences of the trigger signal.

19. The system as claimed in claim 18 wherein each of said remote units and said processing unit comprise a programmable controller and program code stored on a non-transient computer readable media, said program code operating the programmable controller, wherein the same program code is used with said processing unit with each of said remote units.

20. The system as claimed in claim 17 wherein said processing unit synchronizes with each of said sensor units.

21. The system as claimed in claim 20 wherein said processing unit confirms receipt of a trigger signal from one of said sensor units.

22. The system as claimed in claim 21 wherein each of said sensor units receives a trigger signal from the other of said sensor units but does not confirm receipt of the received trigger signal.

23. The system as claimed in claim 17 wherein each of said remote wireless transceivers is configured to mount to a portion of the user's leg or foot.

24. The system as claimed in claim 11 wherein said switches comprise mechanical switches.

* * * * *

UNITED STATES PATENT AND TRADEMARK OFFICE
CERTIFICATE OF CORRECTION

PATENT NO.         : 8,968,218 B2                                           Page 1 of 1
APPLICATION NO.    : 12/703353
DATED              : March 3, 2015
INVENTOR(S)        : Matthew Wukasch and Jose Hernandez, Jr.

It is certified that error appears in the above-identified patent and that said Letters Patent is hereby corrected as shown below:

In the claims
Column 9
Line 4, Claim 14, "11" should be --13--
Line 10, Claim 16, "11" should be --13--
Line 13, Claim 17, "11" should be --13--

Column 10
Line 19, Claim 24, "11" should be --13--

Signed and Sealed this
First Day of March, 2016

Michelle K. Lee
*Director of the United States Patent and Trademark Office*